US010624714B2

(12) United States Patent
Seto (10) Patent No.: US 10,624,714 B2
(45) Date of Patent: Apr. 21, 2020

(54) RADIOPAQUE PROCEDURE SITE MARKER AND METHOD FOR INTRAOPERATIVE MEDICAL IMAGING

(71) Applicant: Target Tape Inc., Surrey (CA)

(72) Inventor: Nicholas Drake Seto, Surrey (CA)

(73) Assignee: Target Tape Inc., Surry, British Columbia (CA)

( * ) Notice: Subject to any disclaimer, the term of this patent is extended or adjusted under 35 U.S.C. 154(b) by 353 days.

(21) Appl. No.: 15/790,155

(22) Filed: Oct. 23, 2017

(65) Prior Publication Data

US 2018/0116757 A1 May 3, 2018

Related U.S. Application Data

(60) Provisional application No. 62/413,664, filed on Oct. 27, 2016.

(51) Int. Cl.
| | |
|---|---|
| *A61B 17/00* | (2006.01) |
| *A61B 90/00* | (2016.01) |
| *A61B 90/94* | (2016.01) |
| *A61B 46/20* | (2016.01) |
| *A61B 1/307* | (2006.01) |

(Continued)

(52) U.S. Cl.
CPC .............. *A61B 90/39* (2016.02); *A61B 1/307* (2013.01); *A61B 6/0492* (2013.01); *A61B 6/12* (2013.01); *A61B 6/487* (2013.01); *A61B 17/00234* (2013.01); *A61B 34/20* (2016.02); *A61B 46/20* (2016.02); *A61B 90/94* (2016.02); *A61B 6/4441* (2013.01); *A61B 2046/205* (2016.02); *A61B 2090/0807* (2016.02); *A61B 2090/374* (2016.02); *A61B 2090/376* (2016.02); *A61B 2090/3764* (2016.02); *A61B 2090/3937* (2016.02); *A61B 2090/3966* (2016.02); *A61B 2090/3983* (2016.02); *A61B 2090/3991* (2016.02)

(58) Field of Classification Search
CPC ........... G09F 3/10; A61B 90/90; A61B 90/39; A61B 2090/08021; A61B 2090/3937
See application file for complete search history.

(56) References Cited

U.S. PATENT DOCUMENTS

| | | | | |
|---|---|---|---|---|
| 2002/0157293 | A1* | 10/2002 | Berryman | A01K 11/005 40/586 |
| 2002/0179094 | A1* | 12/2002 | Perlow | A61B 90/39 128/897 |

(Continued)

*Primary Examiner* — Samuel G Gilbert
(74) *Attorney, Agent, or Firm* — Hancock Hughey LLP (57) ABSTRACT

An apparatus and method that provide an improved method of marking a patient requiring an endourologic procedure such as an ureteroscopy are disclosed. The apparatus is an adhesively-backed sheet with a radiopaque marking symbol designed to eliminate risk of a wrong site surgery by creating a visible, unambiguous marking symbol on an intraoperative medical image. The marker sheet is removably applied to the correct side of the patient's body on the groin or abdomen area before the patient is draped for surgery. The marker is visible to the naked eye before it is covered by drapes and visible on an X-ray or other intra operative imaging device whether covered by drapes or not. The visible marking symbol indicia on the X-ray will be unambiguous and will communicate whether the procedure should or should not be performed on that location.

11 Claims, 4 Drawing Sheets

(51) Int. Cl.
*A61B 6/12* (2006.01)
*A61B 34/20* (2016.01)
*A61B 6/00* (2006.01)
*A61B 6/04* (2006.01)

(56) References Cited

U.S. PATENT DOCUMENTS

| | | | |
|---|---|---|---|
| 2003/0182815 A1* | 10/2003 | Carlson, II | G06K 19/04 33/566 |
| 2004/0056477 A1* | 3/2004 | Bruce | G09F 3/10 283/81 |
| 2004/0056478 A1* | 3/2004 | Bruce | G09F 3/10 283/81 |

* cited by examiner

RADIOPAQUE PROCEDURE SITE MARKER AND METHOD FOR INTRAOPERATIVE MEDICAL IMAGING

TECHNICAL FIELD

The present invention relates generally to apparatus and methods used in surgery. More particularly, the present invention relates to apparatus and methods for improved surgical site skin marking of a patient undergoing an endourology procedure in order to reduce the risk of wrong site surgery.

BACKGROUND OF THE INVENTION

The use of marking pens on surgical patients prior to surgery is common. A surgeon will often use pens to mark lines or designate areas on a patient's body so as to know the proper place for an incision or other surgical procedure that will be performed during the operation. In such cases, it is extremely important that the incision or procedure site be at the correct location. However, with the use of these marking pens, certain specific procedures can result in drapes covering the pen marking and therefore the site marking is no longer visible to the surgeon's eye.

Intraoperative medical imaging (i.e. imaging that occurs within the operating room) is frequently used by a physician to help plan and perform their procedure accurately and efficiently. Intraoperative imaging can assist with identifying the procedure site and guiding the physician during the procedure. Various imaging modalities can be utilized, including, but not limited to: fluoroscopy (also referred to as a "c-arm"), plain X-ray, CT and MRI. The term "medical imaging" is herein used in its broadest sense and "intraoperative imaging" refers to medical imaging that occurs within the operating/procedure room.

Wrong site surgery ("WSS") can be a devastating event with profound medical, legal, and social ramifications. The term "wrong site" can include the wrong site, side, limb, level, organ, or patient. The term "surgery" can also include medical procedures that do no utilize an incision, such as ureteroscopy. WSS is also defined as a sentinel event (i.e., an unexpected occurrence involving death or serious physical or psychological injures, or the risk thereof) by the Joint Commission ("JC", also formerly called the Joint Commission on Accreditation of Healthcare Organizations), which found WSSs to be the third highest ranking event.

Although termed a "never event" in the medical community, WSS continues to occur. The JC and the World Health Organization ("WHO") have each launched a surgical checklist/protocol to help reduce the risk of performing a WSS. The JC's universal protocol includes 3 parts: (a) preoperative verification; (b) marking of the operative site; and (c) a "time-out" immediately before starting the procedure.

The second element of the universal protocol is marking the operative site. Although the JC allows any member of the team to mark the site, ideally it should be done by the physician that performs the procedure. This is required whenever the procedure involves a bilateral distinction or when multiple structures or different levels are involved. It is not required for sternotomy, cesarean section, or laparotomy/laparoscopy, unless right or left organs are involved. Some exclusions also include (a) patient refusal to be marked; (b) cases in which it is technically or anatomically impossible or impractical to mark the site; (c) minimal access procedures to treat a lateralized internal organ, whether percutaneous or through a natural orifice (the intended side is marked at or near the insertion site); (d) interventional procedures for which the catheter or instrument insertion site is not predetermined; and (e) teeth. It should also be noted that not all medical facilities follow the JC or WHO checklist. A facility may also choose to mark the incorrect site that the procedure is not to occur on.

Some surgical procedures do not require an incision, such as an ureteropscopy. An urologist will insert an ureteroscope into the urethra and pass it through the bladder and the ureter, to get to where the kidney stone, or other target, is located. The kidney stone, or target, is then removed or treated.

Although each medical facility may have their own protocols in place, in general, each facility will perform their ureteroscopy procedure in similar steps. The patient is first identified in the holding area according to the preoperative verification step of the universal protocol. The laterality is confirmed by verification with the patient and confirmation of the preoperative radiologic images. The physician then marks the correct side with an indelible marker in the groin or abdomen area. This marking can vary depending on a facility's protocol, but usually consists of either an "X", checkmark, the word "Yes", or the operating physician's initials. The patient is later brought into the operating/procedure room where anesthetization, draping and other pre-procedure prepping events occurs. A "time-out" is performed before the procedure starts to confirm with the medical team the correct patient identity, correct site and correct procedure to be done. This confirmation is usually verbal or via filling out a checklist. The invasive portion of the ureteroscopy procedure can then begin.

Certainty is needed for an ureteroscopy not only to acknowledge the correct intended side, but also to ensure the procedure is actually performed on the correct intended side. The problem with the universal protocol and its possible modifications a facility may incorporate, with respect to endourologic procedures, is that the site marking is no longer visible once the patient is draped; the site marking does not appear on the medical image; and a physician can become confused with the patient and/or medical image's orientation.

The WSS prevention mark is made before the patient enters the operating room because it is suggested to include the patient in this process. Although this indelible mark remains on the patient, usually on the groin/abdomen area, the mark is eventually covered by surgical drapes before the procedure begins. The patient is completely draped except for a small opening over the genital area because the procedure is done through the urethra. Draping defeats the purpose of marking the patient because the physician can no longer see the mark on the body. The mark is also not visible on intraoperative medical imaging.

The indelible marker used by the physician can be a surgical marker, such as something gentian violet based (ex. a Viscot Medical LLC Surgical Marker), or something as common as a Sharpie. This marker is highly visible to the eye, however, does not appear on a medical image scan because the ink is not radiopaque. If the mark is neither visible on the patient's body or the intraoperative medical image scan, then marking the patient's skin is moot.

During the pre-operative stage of the universal protocol checklist, the correct procedure and site is confirmed. This can be noted on the checklist as an "ureteroscopy on the left ureter". An ureteroscopy is commonly performed with the surgeon located between the patient's spread legs, with the patient positioned supine and the physician facing the patient. Confusion can occur with orientation because the patient's left ureter is on the physician's right side. If the medical image is set to mimic the orientation that the physician is experiencing while between the patient's legs, the left side of the patient will be on the right side of the screen. However, the physician or technician may also inadvertently flip the displayed image. This would result in the patient's left kidney on the left side of the image, but the procedure is being performed on the physician's right hand side.

Due to the relatively small image size, there may also be a lack of anatomic detail on fluoroscopy for orientation and to distinguish between the patient's left and right side. Furthermore, as vision is often limited to what is on the image's video screen, others in the operating room do not have the ability to determine which side of the patient the procedure is being performed on.

It is more natural for a person to autonomously think a left side procedure is performed in the direction of their left side, and viewing the medical image to think that the left side of the image correlates to the left side of their patient. Although a physician is trained to overcome orientation confusion, mistakes still occur as 20% of wrong site surgery is urologic.

A technique some facilities utilize to mark the correct side of the body is to use a colored band around the patient's wrist or ankle and have it sticking outside of the drapes. The surgeon can reference the colored band as a redundancy to confirm the correct procedure side. The problem with this is that patient is no longer fully draped and part of their body that should be covered is now exposed. In addition, the colored band, whether on the ankle or the wrist is beyond the procedure area and requires the surgeon to remember to look for a marking that is not on the procedure area they are focused on. A band around the ankle will be behind the surgeon because they are performing the procedure between the patient's spread legs. This requires the surgeon to perform an added step of turning around to view the colored band. It is ideal to mark the correct side by having the site marking within the procedure area.

Prior art methods have utilized radiopaque adhesive markers to label the patient. "Prevention of Wrong Site Surgery During Upper Tract Endoscopy" by Warren et al. utilized self-adhesive disposable radiopaque stickers by Beekley Medical. These radiopaque stickers are visible during intraoperative imaging and labeled with the letter "R" or "L", to mean "right" and "left" respectively. The "R" is adhered to the right side of the patient and the "L" is adhered to the patient's left side. Although this labels the patient's right and left side and helps with orienting the patient, this is an ambiguous technique because it does not label which is the correct site to operate on. These labels also lack the ability to standardize a consistent marking system implemented by the physician or medical facility. The surgeon's usual technique may be to write the word "Yes" on the correct site, however, some procedures would have the "R" or "L" markings. This can lead to confusion because some procedures will have different markings.

It is unclear if a unilateral procedure suggests having both the "R" and "L" adhered, or only a single marker. The images show a single "L" for a left ureteroscopy procedure and both an "R" and "L" for a bilateral ureteral procedure. It can be confusing in the sense that it is unclear which the intended target side(s) is/are. A single "L" marker on the patient's left side could be interpreted that it is the left side that needs treatment, due to there being a lack of an "R" marker. However, it can be interpreted that the single "L" marker is just a reference point to provide clarity on orientation. It can be confusing in the sense that a physician can think of this as a reference direction to inform them of the patient's left side so they can then identify the remaining directions based on the location of the "L" marker. This is analogous to a map showing only the direction of North and relying on the user to identify remaining directions; while such marking may be sufficient on a map because everyone is familiar with compass rose directions it is ambiguous when it comes to patient marking and the physician does not have 100% clarity on the correct procedure side(s) with this method.

It is a general norm when a plain X-ray is taken in radiology (outside the operating room), that an "R" or "L" radiopaque marker is placed. For example, a single hand scan may have an "R" marker on the image to label it as being the right hand. This does not mean a procedure needs to be done on the right hand, it only labels that it is the right hand in the scan image. A chest X-ray may contain a single "R" or "L" marker on the correct side to identify the correct orientation of the patient. For example, having an "L" marker on a chest X-ray does not necessarily mean that there is an issue with the patient's left side.

It is second nature for a surgeon to think an "R" or "L" marker as an orientation reference of the X-ray image. If only a single body part is identified, such as a hand, the surgeon generally interprets the "R" or "L" marker on the image as identify which side the body part belongs to. The authors are now expecting the surgeon to have multiple meanings for the "R" and "L" symbols, one being that it could identify the correct site(s)/side(s) and a second as simply labeling which body part is being imaged.

Having multiple meanings creates risk of error. For example, the initial preoperative X-ray image may scan both the right and left kidney for diagnostic purposes. An "L" marker may be placed on this preoperative scan image to provide a reference of the patient's orientation. If the treatment site is the right kidney and a single "R" sticker is placed on the right side before treatment, the physician is reliant on two different interpretations. The surgeon may recall from memory seeing an "L" on the patient's scans and inadvertently perform the procedure on the left side. This could occur if the c-arm does not image the right side, because the viewing area of a c-arm could be much smaller than a plain X-ray. So if the surgeon does not see the "R" sticker, a WSS could occur. In addition, if the diagnostic image is available in the operating room, the surgeon would see the "L" sticker. If the "R" sticker was placed on the right side of the patient and signaled that was the intended procedure side, the surgeon could be confused because the see an "L" sticker on one image and an "R" sticker another image. This ambiguity creates risk of a WSS.

In the scenario that both the patient's left and right side is labeled with these radiopaque stickers, it brings up similar uncertainty as described above. The physician can interpret this as simply labeling which sides are the patient's left/right and each label does not necessarily validate that both sides require treatment. It can also be interpreted that both sides need treatment because two marks are present.

Although it is recommended that the physician directly apply the sticker, therefore assuming the above described confusion would not occur because the applier is aware of their intentions, because no definitive system is described, it is relied on each individual physician to implement their own method and to remember it. Without a consistent method, there is no certainty that the physician will apply a sticker and recall with 100% certainty if the label means to perform the procedure over the respective marker, or if that marker only labels the patient's orientation.

"Point of Technique: Reducing Wrong-side Errors for Endourology Procedures" by Alleemudder et al. describes a similar technique by Warren et al. Due to the "R" and "L" stickers not being readily available in departments compared to electrocardiography (ECG) tabs, the authors utilized SKINTACT ECG electrode tabs as a radiopaque marker. The ECG tab was placed over the correct procedure side. This removes most of the uncertainty described above, however, the radiopaque item that forms the ECG tab is a small pellet. Using a small pellet, although visible, is not the most user friendly. It can take time for the physician's eye to scan the image until the small pellet is located. It can be especially difficult if the pellet overlaps with a dense bone. The editor also comments that a radiopaque marker is not limited to "R" or "L" stickers or ECG tab. The site can be marked with any "visible" radiopaque marker, such as a paper clip. However, using homemade or non-standardized items creates the possibility of having a system that is not consistent and ambiguous among the medical facility and its staff members. Having individuals perform various different techniques or using different radiopaque markers can create confusion and ultimately exposes the patient to risk of WSS.

The current methods described above demonstrate that there is a distinct need for apparatus and methods that allow a medical professional to visibly mark, on the patient and medical image, the correct site(s)/side(s) of a endourologic procedure in a clear, consistent, unambiguous manner that cannot only be used by a single individual, or throughout a single facility, but also universally in multiple facilities. The apparatus would benefit from a cheap, universal marker specifically designed for an endourologic procedure and further reduces the risk of a WSS.

Other prior art solutions include apparatus and methods of improving surgical site marks. None of the prior art addresses the problems and solutions of overcoming indelible marks that are covered by drapes using unambiguous techniques that can be consistent with a physician or medical facility's protocols in place.

It is an object of the present invention to overcome one or more of the above described drawbacks and/or disadvantages of the prior art apparatus and methods.

SUMMARY OF THE INVENTION

The apparatus and method of the present and illustrated inventions are based on a device that defines an improved means and method of marking a patient requiring an endourologic procedure. As an example, an ureteroscopy procedure will be the sample endourologic procedure described henceforth. The aid is an adhesively-backed marker with a radiopaque marking symbol ("marker") designed to eliminate risk of a WSS by creating a visible, unambiguous marking symbol on an intraoperative medical image. The marker is removably applied to the correct side of the patient's body on the groin or abdomen area before the patient is draped for surgery. The marker is visible to the naked eye before it is covered by drapes and visible on an X-ray whether covered by drapes or not. The visible marking symbol on the X-ray will be unambiguous and will communicate whether the procedure should or should not be performed on that location.

The marker must satisfy three primary constraints to achieve its purpose of producing a marking symbol on an intraoperative medical image while covered by drapes. These three constraints are: at least partially radiopaque marking symbol, unambiguous marking symbol, and attachment to the skin. Once these three constraints are met, additional features and benefits may be included to produce preferred embodiments that are user friendly and economical.

There are several possible marker embodiments and visual symbols. In one embodiment, the marker's symbol is a large "X" that ranges from 0.5-2.0 inches in height. In another design, the marker's symbol is a large "checkmark" that is 0.5-2.0 inches in width. The symbols could also spell "YES" and/or "NO". The marker also has the ability to come in custom symbols based on a physician, facility or regulating body's needs.

The marker could be a circular, rectangular or square shape that contains a skin safe adhesive that is strong enough to remain adhered to the patient from the preoperative area, into the operating room, and during the procedure. The marker could also have a sufficient area of blank space near the visual symbol for the physician to write their initials or other notes on.

The marker will create an easy to view image of its symbol on the medical imaging scan. The side or area that the marker is over will mean that is the intended side/site that the procedure is to be performed on, unless the symbol, physician or facility intentionally determines otherwise.

In accordance with another aspect of the invention, a preferred method for use of the apparatus comprises the following summarized steps:

a. identifying a patient undergoing a procedure that will have its standard indelible skin mark covered by drapes in the procedure room before the invasive portion begins;

b. adhesively attaching a second side of a flexible substrate to the correct procedure side and X-ray visible area of a subject's skin, wherein the substrate includes a marking symbol of at least a partially radiopaque material;

c. performing an intraoperative X-ray image after the patient is draped and prepped; and     d. referencing the mark(s) that appear on the X-ray scan image and performing the procedure on the side that identifies the correct site.

Accordingly, several objects and advantages of the invention are: to provide a visible and unambiguous marking symbol(s) on an X-ray image; to identify correct or incorrect procedure site(s); and prevent wrong site surgery in procedures that have traditional marks obscured by drapes. Other objects and advantages of the present invention, and/or of the currently preferred embodiments thereof, will become more readily apparent in view of the following detailed description of the currently preferred embodiments, other embodiments, and accompanying drawings.

BRIEF DESCRIPTION OF THE DRAWINGS

Further features and advantages of the present invention will become apparent from the following detailed description, taken in combination with the appended drawing, in which.

DETAILED DESCRIPTION OF PREFERRED AND ILLUSTRATED EMBODIMENTS

The invention will now be described with reference to the drawings. The embodiments disclosed herein are to be considered exemplary of the principles of the present invention and various equivalent modifications will be apparent to those skilled in the art based on the teachings herein without departing from the scope or spirit of the invention described in the specification or in the claims.

The term "marking symbol" is used herein to mean without limitation any desired graphic, character, alpha, numeric and/or alphanumeric combination and in any language that is suitable for use in a manner that would clearly indicate the correct or incorrect site of the surgical procedure. It should also be appreciated that any alpha, numeric, or alphanumeric image, phrase or term may further be configured in any desired font, including without limitation, such fonts as Times New Roman, Courier, Ariel and the like as well as in conjunction with any one or more special effect such as bold face print, all capital letters, italics, underlined text, and the like.

Figure 1:
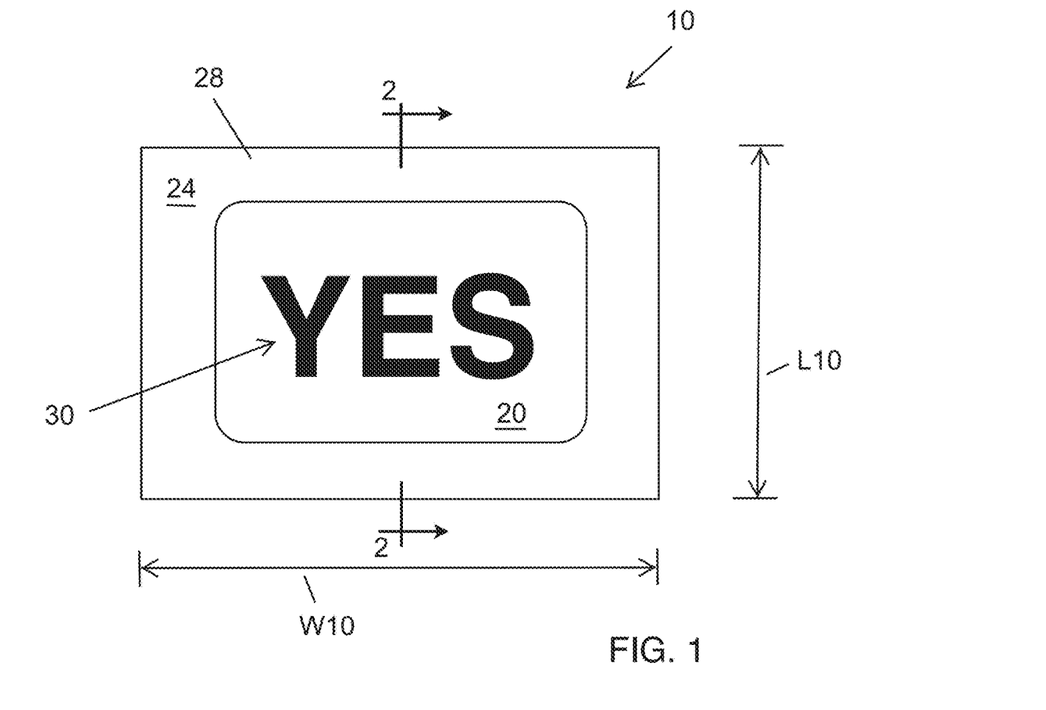
FIG. 1 is a top plan view of a first illustrated embodiment of a marker according to the invention.
Figure 2:
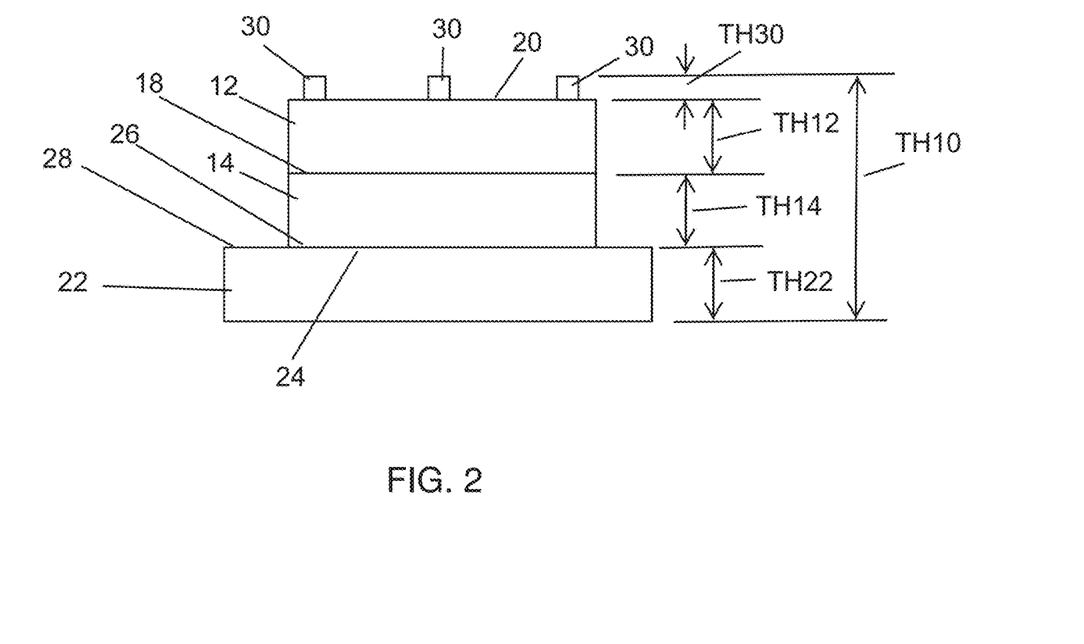
FIG. 2 is a cross sectional view of the marker shown in FIG. 1, taken along the line 2-2 of FIG. 1, and in which the thickness of the layers of the marker is exaggerated in order to better illustrate the invention.

In FIGS. 1 and 2 a radiopaque procedure site marker aid is indicated generally by the reference numeral 10—referred to at times as "marker 10" and "aid 10". The procedure site marker aid 10 comprises a sheet of flexible material that is adapted for conformational adherence to a patient and is defined by a substrate or label layer 12 that has an upper surface 20 and an opposite, lower surface 18. A pressure sensitive adhesive layer 14 is attached or applied to the lower surface 18 of the substrate layer 12 and as seen in FIG. 2, the adhesive layer 14 is coextensive in dimensions with the substrate layer. The aid 10 includes an adhesive-protective release liner 22 that is releasably attached at an upper side 24 thereof to the underside 26 of the adhesive layer 14. The release liner 22 can be larger than the substrate layer 12 and this creates a tab 28 that allows the user to easily separate the substrate 12 from the release liner 22.

As a naming convention, for purposes herein the "first" or "upper" side of the substrate layer 12 is exposed when the aid 10 is in use and hosts a marker symbol 30 that is comprised of material that is at least partially radiopaque to X-ray imaging or other medical imaging modalities. This "first" or "upper" surface 20 faces away from the patient when the aid 10 is in place on the patient. The "second" or "lower" surface 18 is the surface that is opposite surface 20. That is, lower surface 18 is the surface onto which the adhesive layer 14 is applied and in use with a patient, the lower surface 18 is the surface of aid 10 facing the patient's body.

In the embodiment in FIGS. 1 and 2, the aid 10 is substantially rectangular in shape with rounded corners. The aid 10 generally defines, but is not limited to, a width W10 that is preferably about 1 inch and a length L10 of ⅝ of an inch. The aid 10 also defines a thickness TH10 within the range of about 3.0 mils to about 10.0 mils. However, as will be appreciated by those of ordinary skill in the art, other site marker aid size and thickness may also be utilized according to the desired application area, such as, for example, the part of the body to which the aid is to be applied.

Both the substrate layer 12 and the adhesive layer 14 are sufficiently flexible to conformably place the aid 10 atop an underlying curvilinear and irregular surface topography, e.g., the skin surface of a patient, substantially without wrinkling, folding, buckling, distorting or gapping between the aid 10 and the skin surface. The adhesive layer 14 comprises a suitable adhesive that is sufficiently distributed over the lower side or lower surface 18 of the substrate layer 12 in a sufficient amount to sufficiently hold the aid 10 to the contours of the skin surface, e.g., substantially without wrinkling or leaving gaps there between.

As noted above, in some embodiments the substrate layer 12 further includes a marking symbol 30 comprised of a material that is at least partially radiopaque. Preferably, the marking symbol 30 is located on the upper surface 20 of the substrate layer 12 relative to the adhesive layer 14, as shown in FIGS. 1 and 2. The marking symbol 30 is preferably defined by indicia that is unambiguous in confirming the correct procedure site. The symbol could also be consistent with the physician's or medical center's standard practice of identifying correct or incorrect procedure sites, resulting in the marking symbol 30 being unambiguous from the physician's perspective only. For example, FIG. 6G shows the symbol "X", which is sometimes used by physicians. This could be interpreted to mean "X" marks the correct location site. However, it could also be interpreted to mean that "X" is the location where the procedure should not be performed. The marking symbol 30 could be ambiguous to an outsider; however, as long as it is consistent to the physician's or medical center's protocol of interpretation, its meaning would be unambiguous from their perspective. It would be important to note that the marking symbol 30 would be consistent with the marking symbol made with an indelible marker for procedures that the aid 10 is not applicable for use. This results in complete consistency so the operating physician does not need to have different symbols for procedures that the aid 10 is used in compared to procedures that do not require the aid 10. In any case, the indicia conveys to the physician or medical professional information that is indicative of the correct site for the medical procedure to be performed.

As noted, the marker symbol 30 is comprised of an at least partially radiopaque material, in order to be visible in a radiographic image or scan, such as a c-arm. In one such exemplary embodiment, the marker symbol 30 material may be formed of a radiopaque ink such as, for example, but not limited to, tungsten non-lead radiopaque ink. One example of a suitable radiopaque ink used for the reference pattern 30 is tungsten non-lead radiopaque ink sold by Creative Materials, Inc. of Ayer, Mass. In some such embodiments, the ink is printed onto the substrate layer 12. The marker symbol 30 material is not limited to a radiopaque ink, but can also be a copper, lead or other radiopaque metal or material that is printed, adhered to or suspended into the substrate 12.

The thickness TH30 of the marker symbol 30 needs to be an appropriate thickness so it is suitably visible on the X-ray image scan. Thickness TH30 can range from about 1.5-10 mils; however, thicknesses TH30 of the symbol 10 can vary and will depend upon the radiopaque material's density. Those of ordinary skill in the art should understand that the thickness of the marking symbol can be selected as appropriate for the intended application.

The aid 10 illustrated in FIG. 1 is comprised of the word "YES" to form the marker symbol 30. It will be appreciated, however, that other symbols or graphics (i.e., "indicia") can be utilized as well. In the illustrated and preferred embodiment, the substrate layer 12 is a polyethylene terephthalate ("PET") material, preferably white in color. However, as should be recognized by those of ordinary skill in the pertinent art based on the teachings herein, the substrate layer 12 may be formed of any material capable of performing the functions of the substrate layer. That is, and as described further herein, the substrate layer 12 is conformal to the skin contour of the patient without unreasonable gaps, and is rigid enough for the user to handle without the label 12 folding or wrinkling upon itself. In some such embodiments, the thickness TH12 of a PET substrate layer 12 is greater than or equal to about 3.0 mils but less than or equal to about 5.0 mils. It should be appreciated that other capable materials of the substrate layer 12 could be greater or less than said thicknesses TH12. A white color allows the physician to easily visualize that the aid 10 is placed on a patient of any skin pigmentation. Other possible substrate materials include, but are not limited to, polyethylene ("PE"), polyurethane ("PU"), polyolefin ("PO") or a paper material.

In the illustrated embodiment of FIG. 2, the pressure sensitive adhesive layer 14 is a skin compatible material. However, as should be recognized by those of ordinary skill in the pertinent art based on the teachings herein, the adhesive layer 14 may be formed of any material capable of performing the functions of the substrate layer. That is, and as described further herein, the adhesive layer 14 adheres instantly to the skin when light pressure applied, is conformal to the skin contour of the patient without unreasonable gaps, remains attached to the patient during normal movement required in surgery, does not cause unreasonable irritation or pain upon removal from the patient, is safe for human contact, and does not compromise the flexibility of the substrate 12. Upon removal of the aid 10 from the patient, the adhesive layer 14 will be removed along with the substrate so that no adhesive material remains on the patient, and with minimal irritation or pain experienced by the patient. In some such embodiments, the thickness TH14 of the adhesive layer 14 is preferably greater than or equal to 1.0 mils but less than or equal to 3.0 mils.

In the illustrated embodiment, the bond force of the adhesive layer 14 to the lower surface 18 of substrate 12 is greater than the bond force to an underlying surface, such as a patient's skin, upon which the aid 10 is adhered using adhesive layer 14. Accordingly, the adhesive layer 14 substantially does not separate from the substrate 12 when the release liner 22 is removed from the aid 10 or when the aid 10 is removed from the patient's skin.

In the illustrated embodiment of FIG. 2, an example of a preferred substrate 12 and adhesive layer 14 combination is FLX061680 Dermaflex PM 200 White PTP H-566 DR300POLY Matte sold by FLEXcon COMPANY, Inc. of Spencer, Mass. Such a material is easy for a user to handle without the aid 10 wrinkling or folding upon itself; conforms to an underlying curvilinear surface contour substantially without wrinkling, folding, buckling, distorting or gapping between the aid 10 and the surface onto which the aid is adhered; remains attached to the patient during normal movement required in surgery; and does not cause unreasonable irritation or pain upon removal from the patient.

As noted above, the release liner 22 is an adhesive-protective layer that is removably adhered to the lower surface 24 of adhesive layer 14. One purpose of the liner 22 is to protect the adhesive layer 14, e.g., until the aid 10 is about to be used. In some embodiments, the liner 22 is a polymer-based material, such as, for example, but not limited to, a polyester liner. In some embodiments, the liner 22 defines a thickness TH22 (FIG. 2) within the range of about 2.0 mils to about 5.0 mils, which has been found to adequately protect the adhesive layer 14. Other suitable materials and thicknesses can also be used. While the liner 22 is intended to remain on the adhesive layer 14 until use, it also can be removed without excessive difficulty. For easier separation from the adhesive 14, the release liner 22 is larger than the substrate layer 12 in one or more area(s). This creates a tab 28 where the release liner 22 extends beyond the periphery of substrate layer 12, providing the user with an efficient method to separate the substrate layer 12 from the release liner 22.

Figure 3:
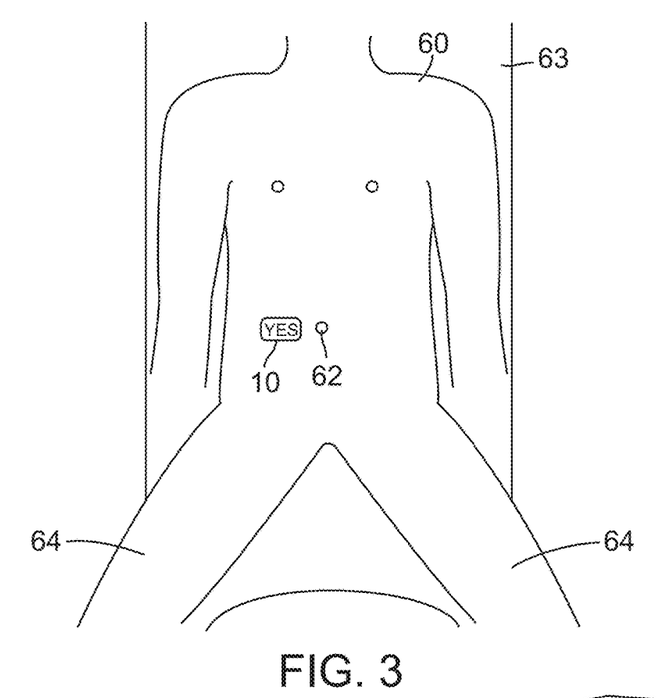
FIG. 3 is a top plan view of a patient in a supine position on a surgical table with legs spread apart in preparation for a surgical procedure and in which a marker according to the invention is applied to the patient's abdomen over the correct procedure side.

With reference to FIG. 3 and as discussed above, the procedure marking aid 10 can be used for urology surgery, specifically ureteroscopy that utilizes a c-arm. In one exemplary embodiment, the aid 10 is placed on a patient 60 to assist a urologist in creating a surgical site marking that is visible on the X-ray image after the patient is draped. The aid 10 is preferably placed approximately 1.5-2.0 inches left or right of the naval 62. The aid will preferably be placed over the correct site with a symbol that reasonably communicates this, however, a corresponding aid could also be placed over the incorrect site with a reference symbol that reasonably indicates the incorrect site (see, for instance, FIG. 6F in which the indicia comprising marker symbol 30 is the word "NO").

Figure 4:
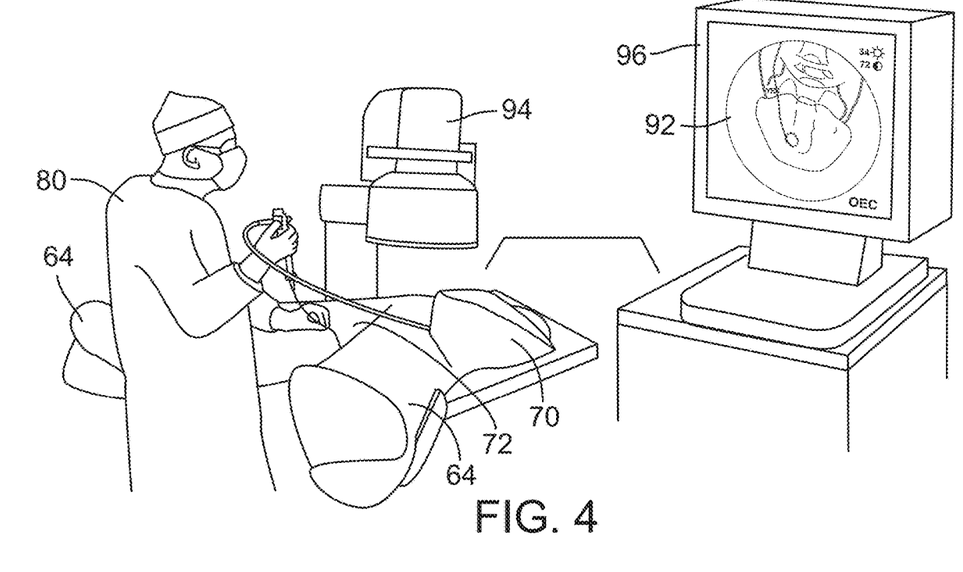
FIG. 4 is a perspective and schematic view of a typical operating room in which a patient is lying in a supine position as shown in FIG. 3 with the patient draped with surgical drapes, and in which a surgeon is positioned between the patient's spread-apart legs and performing a procedure on the patient; the surgeon is viewing the intraoperative medical image on a computer monitor.

FIG. 4 illustrates the setup of an ureteroscopy procedure in the operating room. The patient 60 is in a supine position with their legs 64 spread apart and their body completely covered with surgical drapes 70 except for a small opening hole 72 over the genital area. An intraoperative c-arm 94 surrounds the patient over the procedure area. The surgeon 80 is between the patient's spread legs 64 and facing the patient's face. This results in the surgeon's 80 right side being the patient's 60 left side and vice versa. The aid 10, along with any indelible ink markings (if any), is occluded from view by the surgical drapes and therefore no longer visible to the naked eye because it is covered by the surgical drapes 70. The marking symbol 30 is visible on the c-arm's image 92 (displayed on monitor 96) and guides the surgeon 80 to the correct procedure site.

Figure 5A:
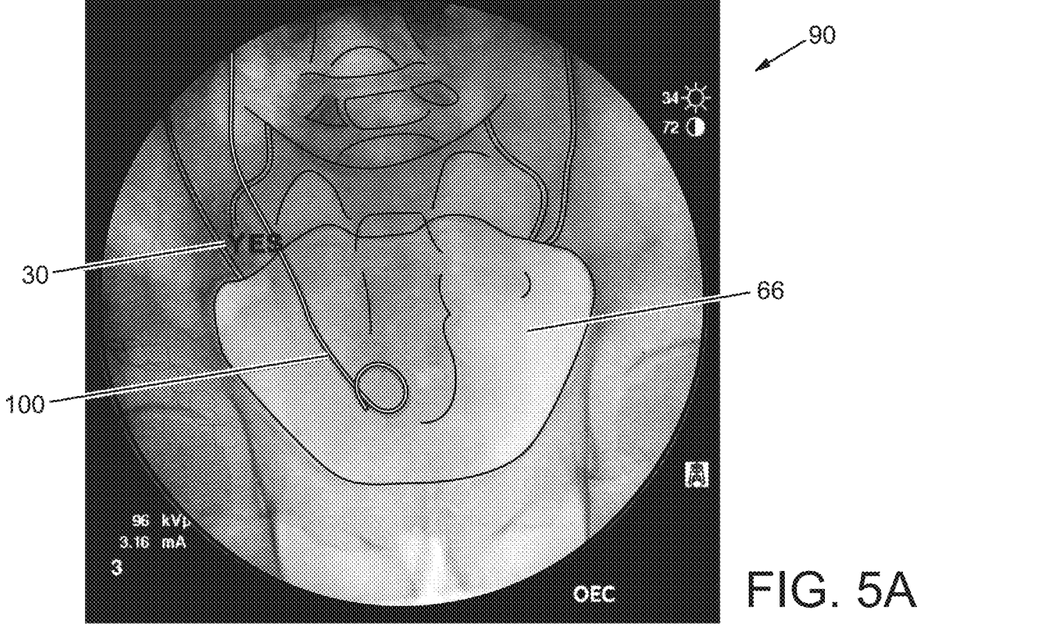
FIG. 5A is an intraoperative radiographic image of a c-arm scan, showing the patient's bladder and ureters, the bottom portion of an inserted double JJ stent, and the marking aid according to the invention.
Figure 5B:
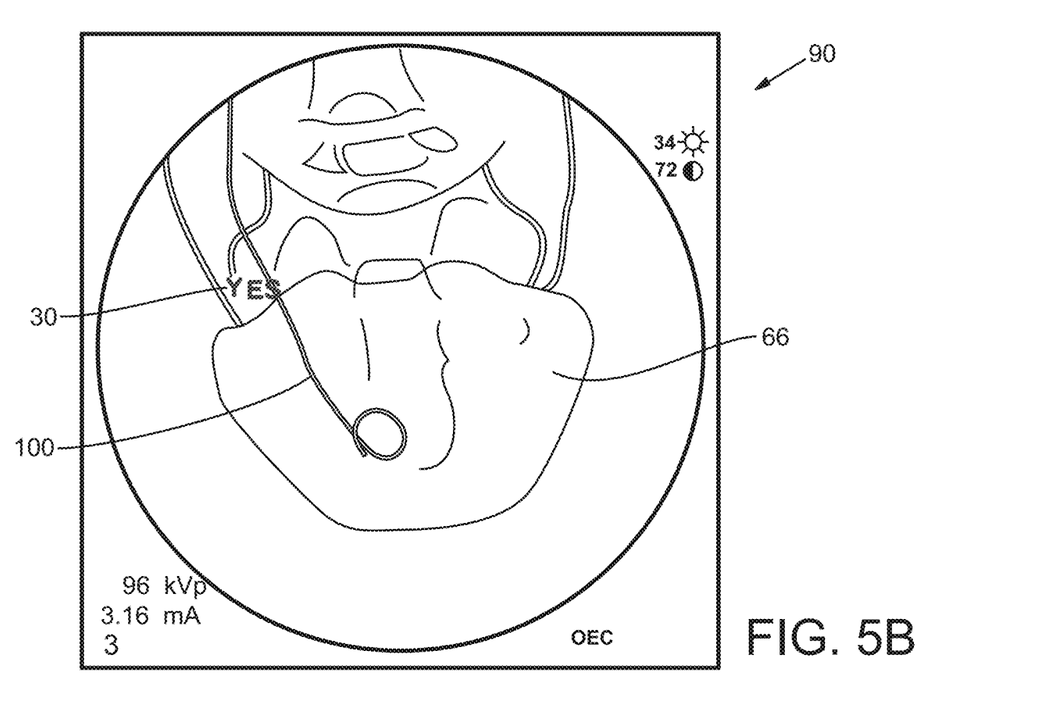
FIG. 5B is a schematic representation of the radiographic image shown in FIG. 5A.

FIG. 5A is an actual intraoperative scan image, with reference number 90, of the aid 10 attached to a patient's body in the location shown in, for example FIG. 3. FIG. 5B is a schematic drawing of the intraoperative scan shown in FIG. 5A. The drawings of FIGS. 5A and 5B are typical intra operative scans and illustrate what is displayed with a c-arm scan used in during surgery. The scan image 90 shows the patient's bladder 66 and a double j stent 100 that is inserted through the bladder 66, into the patient's right ureter. The marking symbol 30 appears on the scan image 90 because of its radiopaque nature. If any pen markings were drawn on the patient, these markings will not show up on the X-ray image 90 because it is not radiopaque. The marking symbol 30 shows the word "YES" to indicate the correct side that the procedure is to be performed on. In this example, the aid 10 was applied over the patient's right side, which corresponds to the surgeon's left side when the surgeon is positioned between the patient's legs as in FIG. 4. The marking symbol 30, with its procedure affirmative message on the image 90, eliminates any ambiguity or right/left confusion as the surgeon would only need to direct their hardware towards the side that the marking symbol 30 appears on the image 90. Ideally, the marking symbol 30 "YES" is a consistent message for the physician/medical center to indicate the correct procedure site for procedure's whose pen markings are not covered by drapes.

Figure 6:
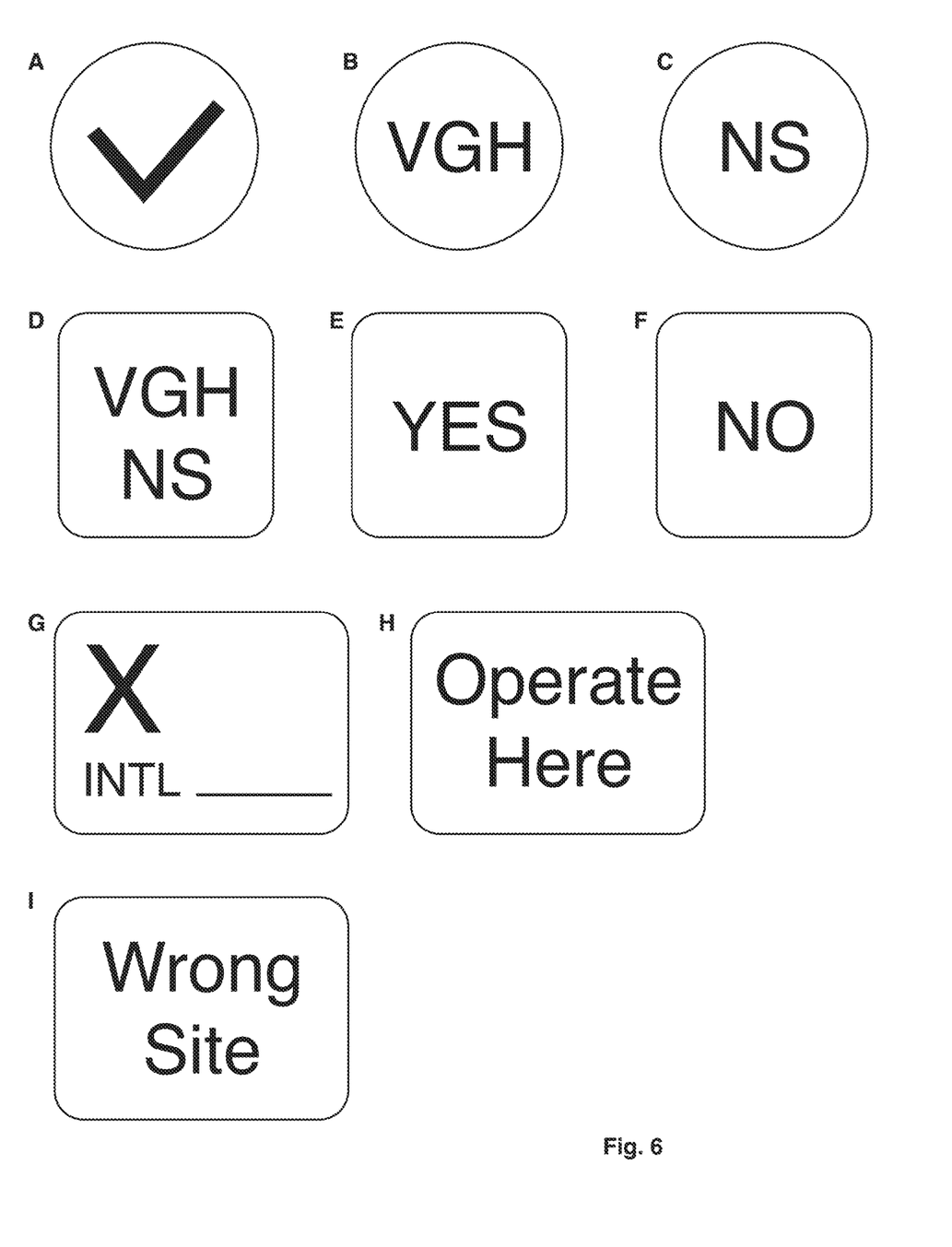
FIG. 6 shows various alternative embodiments of a marker according to the present invention.

FIG. 6 illustrates various different radiopaque marker symbols. These marker symbols can be customized to the physician's or medical center's standard marking message so all markings are consistent throughout all procedures. Each facility may have their own unique protocols and symbol meanings. The marker is flexible in accommodating their established systems and/or symbols. As time progresses, there could be regulated protocols to create universal symbols and/or marking requirements. If mandates are put in place, the marker can be modified to accommodate virtually any visual symbol and its interpreted meaning. The marker can also come in various sizes and shapes to accommodate spacing requirements, as some physicians may prefer to sign their initials on the marker.

FIG. 6A is a "checkmark", which generally means "correct". Some individuals may interpret the checkmark as "good", i.e. this is the good, non-operative site, do not operate here. However, a check mark can be illegible and interpreted as a "V", "Y", "U" or perhaps even a sloppy "X". With possible illegibility, a physician can be confused.

FIG. 6B illustrates a facility's initials. In this example, "VGH" stands for "Vancouver General Hospital". The facility's initials would generally be placed over the correct site/side.

FIG. 6C illustrates the physician's initials. Initials are used by many medical facilities to mark the correct side, in addition, other symbols may also be included. In this example, "NS" stands for the inventor's name, "Nicholas Seto". It is generally accepted that the procedure site contains the physician's initials. It is also generally accepted that the person marking the site provides their initials. If for some reason the physician is not present to mark the site, then a nurse may mark the site with their initials. This is to provide accountability in case an error is made.

FIG. 6D illustrates a combination of the facility's initials and the physician's initials, as shown in FIGS. 2B and 2C. This is to create accountability for both the medical center and the physician.

FIG. 6E illustrates the word "YES" as being the symbol. This has been generally accepted as being marked on the site/side where the procedure is to be performed. For example, Viscot Medical, LLC of East Hanover, N.J. provides a correct site Tat Marker tattoo that only comes in the symbol "YES". It is intended to be placed over the correct procedure site/side. The "YES" symbol can also be substituted with only the letter "Y".

FIG. 6F illustrates the word "NO" as being the symbol. For added redundancy and clarification, using the "NO" symbol could also be used alongside the "YES" symbol. This adds further clarification that the physician is on the incorrect area if the "NO" symbol appears on the intraoperative medical image. The "NO" symbol can also be substituted with an "N".

FIG. 6G illustrates the letter "X" and an area of blank space for the individual placing the aid 10 on the patient to sign their initials on the aid itself. This reduces the amount of customization because printed initials are not needed for individual medical staff. It should also be noted that the blank space to sign initials or add other messages are not limited to being in combination with the "X" symbol and can be combined with any marker symbol.

FIG. 6H illustrates the phrase "Operate Here", which suggests the correct operating location.

FIG. 6I illustrates the phrase "Wrong Site", which suggests the incorrect operating location.

One skilled in the art will understand that the symbol suggestions of FIGS. 1 and 2 are not limited and can contain a combination of illustrated symbols described above or other symbols not shown.

The method of using an aid 10 will now be detailed with specific reference to the aid 10 as shown in FIG. 1, and with reference to FIGS. 3 through 5. The aid 10 provides a method for non-permanently marking the correct site on a patient 60's body for a surgical procedure that would normally have its regular mark covered by medical drapes 70, the method comprising steps of positioning a radiopaque procedure marker aid 10 with a marking symbol 30 over a predetermined location for a surgical procedure to be performed on a patient, adhering the marking aid 10 onto the patient's body thereby marking the location of a surgical procedure to be performed on the patient, visually viewing the marking symbol on an intraoperative X-ray image, and performing the procedure on the correct site according to the marking symbol's 30 communicative message.

In one aspect, the patient 60 is first positioned supine on the medical bed 63 in the preoperative holding area. The preoperative holding area is not mandatory, but preferred, because this is usually where the patient is marked. The patient 60 confirms the procedure details with their medical professional, usually the operating surgeon. These details can include the type of procedure and the predetermined procedure location site. If the procedure is a type where the surgical site mark will be covered by medical drapes, typically a urological procedure such as ureteroscopy, the medical professional will apply the aid over the correct predetermined procedure site.

Upon application of the aid 10 to the patient 60, the medical professional has the option to sign or initial the site with an indelible marking pen/stamp. This can be done directly on the patient's skin beside the aid 10, or on the aid 10 itself.

Once the patient enters the operating room, they are prepped for surgery. Prepping can include, amongst other tasks, draping the patient which results in covering the aid 10. Thereafter, the c-arm is utilized to image the patient. The resulting aid 10 is visible on the medical image and guides the surgeon to the correct site location. The surgeon can then carry out the procedure and can be confident the correct location is being operated on as their hardware will be visible on the correct location that the marking symbol 30 is visible on.

Accordingly, this detailed description of currently preferred embodiments is to be taken in an illustrative, as opposed to a limiting, sense.

While the present invention has been described in terms of preferred and illustrated embodiments, it will be appreciated by those of ordinary skill that the spirit and scope of the invention is not limited to those embodiments, but extend to the various modifications and equivalents as defined in the appended claims.

The invention claimed is:

1. A method of identifying a correct medical procedure site on a patient undergoing a medical procedure in which the medical procedure is performed using intraoperative medical imaging, comprising the steps of:
- a. identifying on the patient the correct procedure site for the medical procedure;
- b. applying to the patient over the correct procedure site a sheet having indicia thereon comprising material at least partially opaque to intraoperative medical imaging;
- c. covering the patient such that at least the correct procedure site is visibly occluded;
- d. creating an intraoperative image of the patient;
- e. displaying the intraoperative image;
- f. identifying on the displayed image the at least partially opaque material; and
- g. using the displayed image as a reference, performing the medical procedure.

2. The method according to claim 1 in which the indicia conveys information associated with the site for the medical procedure.

3. The method according to claim 2 in which the indicia identifies the correct site for the medical procedure.

4. The method according to claim 3 in which the step of covering the patient such that at least the correct procedure site is visibly occluded includes the step of covering the patient with surgical drapes.

5. The method according to claim 4 in which the medical procedure is an endourologic procedure.

6. The method according to claim 5 in which the medical procedure is ureteroscopy.

7. The method according to claim 1 in which the indicia identifies an incorrect site for the medical procedure.

8. A method of reducing the risk of wrong site surgery arising from a medical procedure when the medical procedure is performed using intraoperative medical imaging and in which the medical procedure site is covered with surgical drapes, comprising the steps of:
- a. applying to a patient over a correct site for the medical procedure site a sheet having indicia thereon comprising material that is at least partially opaque to intraoperative medical imaging;
- b. covering the correct site with a surgical drape so that the correct site is visibly occluded;
- c. creating an intraoperative image of the correct site;
- d. displaying the intraoperative image;
- e. identifying on the displayed image the at least partially opaque material; and
- f. using the displayed image as a reference, performing the medical procedure.

9. The method according to claim 8 in which the intraoperative imaging comprises fluoroscopy.

10. The method according to claim 9 in which the medical procedure is an endourologic procedure.

11. The method according to claim 10 in which the medical procedure is ureteroscopy.

* * * * *